United States Patent [19]

Scheidl et al.

[11] Patent Number: 4,590,302
[45] Date of Patent: May 20, 1986

[54] TERPENE ETHERS

[75] Inventors: Franz Scheidl; Manfred Gscheidmeier, both of Gablingen, Fed. Rep. of Germany

[73] Assignee: Hoechst Aktiengesellschaft, Fed. Rep. of Germany

[21] Appl. No.: 634,403

[22] Filed: Jul. 25, 1984

[30] Foreign Application Priority Data

Jul. 27, 1983 [DE] Fed. Rep. of Germany ....... 3327014

[51] Int. Cl.⁴ ..................... C07C 43/18; C07C 43/196
[52] U.S. Cl. ................ 568/665; 252/522 R; 252/364
[58] Field of Search ....................................... 568/665

[56] References Cited

U.S. PATENT DOCUMENTS 2,360,898 10/1944 Sarbach .......................... 568/665 X
2,388,765 11/1945 Rummelsburg ..................... 568/665
3,354,225 11/1967 Kane ................................ 568/665
3,636,927 1/1972 Baum .
4,521,634 6/1985 Fujioka et al. ....................... 568/665

FOREIGN PATENT DOCUMENTS 2815392 10/1978 Fed. Rep. of Germany .
2815393 10/1978 Fed. Rep. of Germany .

Primary Examiner—Bernard Helfin
Attorney, Agent, or Firm—Connolly and Hutz

[57] ABSTRACT

The invention relates to new terpene ethers of the formula

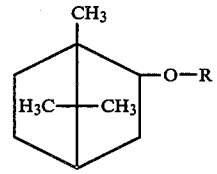

in which R denotes a cyclic or bicyclic radical or an alkyl radical which is substituted by cyclic, bicyclic or tricyclic radicals, optionally via an oxygen bridge. The compounds are prepared by reaction of camphene with alcohols R—OH, in which R represents one of the above-mentioned radicals. The new ethers are used in the field of aroma substances and solvents, and as intermediates for plant protection agents, agents for combating pests and medicaments.

1 Claim, No Drawings

TERPENE ETHERS

Terpene ethers have economic importance, inter alia, as plant protection agents (cf. U.S. Pat. No. 3,871,863) and, in particular, as aroma substances (cf. Japanese Pat. No. 0,142,550; and U.S. Pat. Nos. 3,636,927 and 3,354,225). These terpene ethers are compounds of the general formula

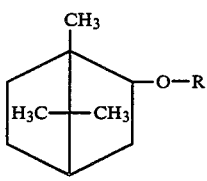

in which R represents the radical of a simple, shortchain monoalcohol or dialcohol or of a derivative of such an alcohol.

It has been found that previously unknown terpene ethers with the same general structure but in which R is the radical of a complicated, sterically critical alcohol, are useful products or intermediates in the context of the abovementioned fields of use and in the sector of fixatives and of solvents.

The invention thus relates to new terpene ethers of the formula

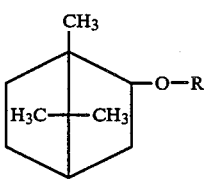

in which R denotes one of the radicals mentioned below:

(a) cycloalkyl which has 5 to 12 carbon atoms and which can be substituted by a radical $-O-R^1$, in which $R^1$ represents H, $C_1$- to $C_{18}$-alkyl, $C_5$- to $C_{12}$-cycloalkyl, $C_7$- to $C_{12}$-bicycloalkyl, or $C_1$- to $C_6$-alkyl which is substitututed by cycloalkyl, bicycloalkyl or tricycloalkyl, (b) bicycloalkyl with 7 to 12 carbon atoms, (c) $C_2$- to $C_{20}$-alkyl, which is substituted by a radical $-O-R^2$, in which $R^2$ denotes $C_5$- to $C_{12}$-cycloalkyl, $C_7$- to $C_{12}$-bicycloalkyl, or $C_1$- to $C_6$-alkyl which is substituted by cycloalkyl, bicycloalkyl or tricycloalkyl, (d) $C_1$- to $C_4$-alkyl which is substituted by $C_5$- to $C_{12}$-cycloalkyl, it being possible for the cycloalkyl radical to carry a substituent $-CH_2-O-R^1$, where $R^1$ is as described under (a), (e) $C_1$- to $C_4$-alkyl, which is substituted by $C_7$- to $C_{12}$-bicycloalkyl, or (f) $C_1$- to $C_4$-alkyl, which is substituted by $C_8$- to $C_{11}$-tricycloalkyl, it being possible for the tricycloalkyl radical to be in turn substituted by $-CH_2-O-R^1$, where $R^1$ is as described under (a),
and a process for their synthesis.

In the terpene ethers according to the invention—1,7,7-trimethyl-bicyclo[2.2.1]hept-2-yl ethers according to IUPAC nomenclature —the 1,7,7-trimethyl-bicyclo[2.2.1]hept-2-yl radical can be in the d-, l- or, preferably, d,l-form and the —O—R radical can be in the exo- and/or endo form.

The new compounds can be prepared by methods which are known per se. Thus, they can be obtained, for example, by the conventional processes for ethers by reacting bornyl and/or isobornyl chloride with the alcohols, or borneol and/or isoborneol with the halides, corresponding to the alcohols, of the formula R—X (X=Cl, Br or I). Needless to say, this process has disadvantages, in particular in the ecologically undesirable halides unavoidably obtained and the formation of by-products. Moreover, if borneol or isoborneol is to be used as the starting substance, it is difficult to provide the halides—especially those derived from complicated alcohols.

A better and thus preferred procedure for the preparation of the new ethers uses inexpensive camphene as the starting substance, which is reacted with the alcohols of the general formula R—OH, in which R has the abovementioned meaning. In the reaction, which proceeds in the presence of acid catalysts according to the equation

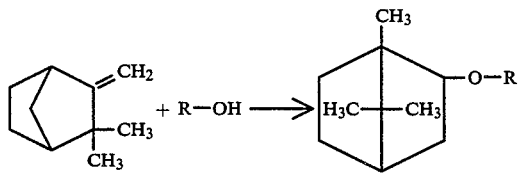

the intermediate step is a Wagner-Meerwein rearrangement of the camphene into a camphane intermediate.

The synthesis is carried out at temperatures between room temperature (20° C.) and 160° C., preferably at 50° to 140° C. and in particular at 70° to 120° C. Depending on the desired product, the reaction partners can be used in equimolar amounts, or an excess of one or other of the partners may also be used.

Catalysts which can be used are mineral acids, such as, for example, sulfuric acid, perchloric acid, phosphoric acid and chlorosulfonic acid, strong organic acids, such as p-toluenesulfonic acid, methanesulfonic acid and camphor-10-sulfonic acid, acid ion exchangers or Friedel Crafts catalysts, such as boron trifluoride and addition products thereof (for example etherates and its glacial acetic acid complex), aluminum chloride, zinc chloride and the like, in amounts of 0.1 to 10% by weight, preferably 0.5 to 6 and in particular 1 to 4% by weight, based on the camphene employed.

The reaction can be carried out in the presence or absence of inert solvents. Examples of suitable solvents are aliphatic hydrocarbons, such as pentane, hexane, benzine fractions, chloroform and carbon tetrachloride, aromatic hydrocarbons, such as toluene, xylene or chlorobenzene, cycloaliphatic hydrocarbons, such as cyclohexane or cyclooctane, and ethers, such as dioxane, dibutyl ether or ethylene glycol dimethyl ether. It is particularly advisable to carry out the reaction without addition of a solvent.

In general, the entire amount of all the reactants, including the catalyst, can be taken for the reaction. In some cases, the reaction proceeds slightly exothermically, so that it is then more advantageous to take the catalyst the alcohol R—OH and to meter in the camphene at the desired temperature.

Examples which may be mentioned of alcohols R—OH which are reacted with the camphene are: cyclopentanol, cyclooctanol, cyclododecanol, cyclohexane-1,2-diol, cyclohexane-1,4-diol and 2-methoxycyclohexanol, compounds where R=(a) being obtained.

Compounds where R=(b) are given by, for example, 3-hydroxy-2,6,6-trimethyl-bicyclo[3.1.1]heptane (pinan-3ol) and 3,7,7-trimethyl-4-hydroxy-bicyclo[4.1.0]heptane (caran-4-ol).

Compounds where R=(c) are obtained by reaction with the following alcohols: ethylene glycol monocyclohexyl ether, propylene glycol mono-pinan-3-yl ether, neopentylglycol, ethylene glycol or ethylene glycol monoisolongifolyl ether.

Compounds in which R denotes (d) are obtained, for example, from camphene and cyclohexane-1,4-dimethanol, cyclohexane-1,4-dimethanolmonomethyl ether or (2,2,3-trimethylcyclopent-1-yl).

The following alcohols, for example, are used for the preparation of compounds where R=(e): 2-hydroxymethyl-6,6-dimethyl-bicyclo[3.1.1]heptane (pinan-10-ol), 2-hydroxymethyl-3,3-dimethyl-bicyclo[2.2.1]heptane (camphanol), 2-(2-hydroxyethyl)-3,3-dimethyl-bicyclo[2.2.1]heptane (homocamphanol) and 2-(2-hydroxyethyl)6,6-dimethyl-bicyclo[3.1.1]heptane.

Finally, possible alcohols for the preparation of compounds where R=(f) are: 4,8,8-trimethyl-9-hydroxymethyl-decahydro-1,4-methanoazulene (isolongifolol) and the commercially available alcohols TCD-alcohol-M: 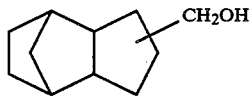 and TCD-alcohol-DM: 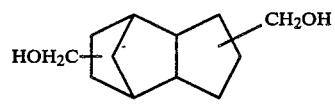

It was in no way predictable that it would be possible to prepare the new compounds at all, even more so under relatively mild conditions; rather, it had to be expected that when the alcohols which, as already mentioned above, are sterically critical are used, either no reaction at all occurs or deviating or side reactions take place. It is therefore surprising that the reaction which is known per se but has hitherto been described for only a few lower alcohols is apparently subject to no restriction in respect of the nature of the alcohol.

After removal of the catalyst (for example washing with water or neutralization by means of bases), the reaction products are in general purified by distillation, but for some intended uses distillation is not necessary. A further possibility of purification is recrystallization from suitable solvents.

The reaction products are low-viscosity to high-viscosity liquids or solid products; they are colorless to slightly yellow-colored.

Some of the new compounds have the pronounced character of an aroma substance and can therefore be used by themselves as fragrances or in a fragrance combination, ie. in mixtures with synthetic and natural oils, alcohols, aldehydes, ketones, esters and the like; they are furthermore suitable for perfuming soaps, detergents, powders, bath oils, hair care agents, creams and other known formulations containing fragrances. Because of their consistency, the majority of the new terpene ethers are useful as fixatives for aroma substances; the compounds suitable here have, as viscous liquids, the property of greatly reducing the volatility of aroma substances. Furthermore, some of the products can be used as solvents, for example for resins and lacquers.

Finally, those representatives of the new ethers which contain free hydroxyl groups are suitable as reactive intermediates, for example for the synthesis of plant protection agents, agents for combating pests and medicaments.

The following Examples are intended to illustrate the invention in more detail.

EXAMPLE 1

A 1 liter three-necked flask equipped with a stirring device, an internal thermometer and a condenser was charged with 272 g (2 moles) of camphene, 430 g (5 moles) of cyclopentanol and 10 g of concentrated sulfuric acid. The contents of the flask were stirred at 100° C. for 24 hours. The mixture was then washed with water at room temperature until neutral, to remove the sulfuric acid. After the excess of cyclopentanol had been distilled off, fractionation of the residue gave a colorless liquid of boiling point 85°C./0.5 mbar and density (20° C.) 0.923.

Yield: 300 g of 1,7,7-trimethyl-bicyclo[2.2.1]hept-2-yl cyclopentyl ether≙67.6% of theory.

Analysis: Molecular weight=220; calculated: 222.
Gas chromatography: 96% pure product.
Smell: Pleasantly fresh, fruity note.

EXAMPLE 2

A mixture of 272 g (2 moles) of camphene and 600 g (3.26 moles) of cyclododecanol was stirred in the presence of 10 g of concentrated sulfuric acid at 100° C. for 24 hours in the apparatus described in Example 1. Working up was carried out as described in Example 1. A yellowish, viscous, odorless liquid of boiling point 165° to 168° C./0.13 mbar and density (20° C.) 0.957 was obtained.

Yield: 126 g of 1,7,7-trimethyl-bicyclo[2.2.1]hept-2-yl cyclododecyl ether≙20% of theory.

Molecular weight: 314; calculated: 320.
Gas chromatography: 92% pure product.

Example 3

272 g (2 moles) of camphene were stirred with 520 g (4 moles) of 2-methoxycyclohexanol in the presence of 5 g of 70% strength perchloric acid at 120° C. for 36 hours in the apparatus described in Example 1. After customary working up, a colorless, almost odorless liquid of boiling point 97 to 100° C./0.5 mbar and density (20° C.) 0.935 was obtained.

Yield: 410 g of 1,7,7-trimethyl-bicyclo[2.2.1]hept-1-yl 2-methoxy-cyclohexyl ether≙74.3% of theory.

Molecular weight: 278; calculated: 276.
Gas chromatography: 89% pure product.

EXAMPLE 4

78 g (0.5 mole) of camphene and 147 g (0.5 mole) of 2-(3,3-dimethyl-bicyclo[2.2.1]hept-2-yl)-ethoxycyclohexanol were stirred in the presence of 3 g of 70% strength perchloric acid at 120° C. for 48 hours under the apparatus conditions described in Example 1. After washing with water and distilling off the volatile constituents up to an internal temperature of 150° C. under a vacuum of up to 13 mbar, a yellowish, viscous, virtually odorless residue was obtained. Density (20° C.)=0.975.

Yield: 173 g of 1.7.7-trimethyl-bicyclo[2.2.1]hept-2-yl 2-(3,3-dimethyl-bicyclo[2.2.1]hept-yl)-ethoxy-cyclohexyl ether=40.2% of theory.

Molecular weight: 426; calculated: 430.

EXAMPLE 5

272 g (2 moles) of camphene were reacted with 308 g (2 moles of pinan-3-ol in the presence of 10 g of boron trifluoride-etherate as described in Example 1. After washing with water and distilling off the highly volatile constituents, a colorless viscous distillate with a pleasantly fruity aroma, a boiling point of 131° to 133° C./1 mbar and a density (20° C.) of 0.985 was obtained.

Yield: 145 g of 1,7,7-trimethyl-bicyclo[2.2.1]hept-2-yl 2,6,6-trimethyl-bicyclo[3.1.1]hept-3-yl ether≐50% of theory.

Molecular weight: 292; calculated: 290.

Gas chromatography: 94% pure product.

EXAMPLE 6

408 g (3 moles) of camphene and 62 g (1 mole) of ethylene glycol were stirred in the presence of 400 ml of toluene, as the solvent, and 5 g of anhydrous aluminum chloride at 80° C. for 30 hours under the apparatus conditions described in Example 1. After washing with water and stripping off the volatile constituents (toluene, excess camphene and ethylene glycol mono-1,7,7-trimethyl-bicyclo[2.2.1]hept-2-yl ether of boiling point 120° to 125° C./13 mbar), a colorless, odorless distillate which crystallizes on cooling and has a boiling point of 168° to 169° C./1.3 mbar was obtained.

Yield: 223 g of ethylene glycol di-1,7,7-trimethyl-bicyclo[2.2.1]hept-2-yl ether=67% of theory.

Molecular weight: 329; calculated: 334.

Melting point: 72° to 75° C.

EXAMPLE 7

136 g (1 mole) of camphene and 198 g (1 mole) of ethylene glycol mono-(3,3-dimethyl-bicyclo[2.2.1]hept-2-yl)-methyl ether was stirred in the presence of 400 ml of carbon tetrachloride and 5 g of boron trifluoridediethyl etherate at 80° C. for 10 hours in the apparatus described in Example 1. After washing with water and distilling off the volatile constituents, a colorless, highly viscous liquid which smells slightly of camphor and has a density (20° C.) of 0.984 was obtained.

Yield: 201 g of 1-(1,7,7-trimethyl-bicyclo[2.2.1]hept-2-oxy)-2-(3,3-dimethyl-bicyclo[2.2.1]hept-2-yl)-methoxy-ethane=60.2% of theory.

Molecular weight: 327; calculated: 334.

Gas chromatography: about 94% pure product.

Example 8

272 g (2 moles) of camphene were stirred with 144 g (1 mole) of 1,4-dimethylolcyclohexane in the presence of 10 g of concentrated sulfuric acid at 100° C. for 24 hours under the apparatus conditions described in Example 1. After washing with water and distilling off the volatile constituents up to 200° C./20 mbar, a yellowish, odorless residue which crystallized at room temperature remained.

Yield: 260 g of cyclohexane-1,4-dimethyl-bis-1,7,7-trimethyl-bicyclo[2.2.1]hept-2-yl ether=62.5% of theory.

Melting point: 43° to 47° C.

Molecular weight: 403; calculated: 416.

Hydroxyl number: 11.

EXAMPLE 9

272 g (2 moles) of camphene were reacted with 640 g (4.44 moles) of 1,4-dimethylolcyclohexane in the presence of 10 g of concentrated sulfuric acid under the reaction conditions described in Example 8. After working up according to Example 8, a yellowish, highly viscous, odorless residue was obtained as the reaction product.

Yield: 373 g of 4-hydroxymethylcyclohexyl-1-methyl-1,7,7-trimethyl-bicyclo[2.2.1]hept-2-yl ether=64.8% of theory.

Molecular weight: 290; calculated: 280.

Hydroxyl number: 212; calculated: 204.

EXAMPLE 10

272 g (2 moles) of camphene were stirred with 624 g (4 moles) of 2-(2,2,3-trimethyl-cyclopent-1-yl)-ethanol in the presence of 12 g of ortho-phosphoric acid at 120° C. for 48 hours in the apparatus described in Example 1. After washing with water and distilling off the volatile constituents, a colorless, pleasantly smelling substance which is crystalline at room temperature and has a boiling point of 135° to 138° C./0.4 mbar was obtained.

Yield: 328 g of 1,7,7-trimethyl-bicyclo[2.2.1]hept-2-yl 2-(2,2,3-trimethyl-cyclopent-1-yl)-ethyl ether=56.2% of theory.

Molecular weight: 287; calculated: 292.

Gas chromatography: about 89% pure product.

Melting point: 30° to 33° C.

EXAMPLE 11

1,664 g (16 moles) of neopentyl glycol (2,2-dimethyl-propane-1,3-diol) and 112 g of boron trifluorideacetic acid complex ($BF_3.2CH_3CO_2H$) were initially introduced into a 10-liter glass flask equipped with a stirrer, an internal thermometer, a condenser and a dropping funnel which could be heated, after which the mixture was warmed to 80° C. 4,352 g (32 moles) of molten camphene were then metered in at 80° to 85° C. in the course of two hours. Stirring was continued at 80° to 85° C. for 20 hours and the reaction mixture was then washed with water until neutral and the unreacted camphene was distilled off in vacuo up to an internal temperature of 120° C. under a vacuum of 50 mbar. A yellowish, viscous, virtually odorless liquid with a density (20° C.) of 0.945 remained as the residue.

Yield: 5,118 g of residue.

Molecular weight: 362; calculated: 376.

Gas chromatography: 80% of neopentyl glycol di-1,7,7-trimethyl-bicyclo[2.2.1]hept-2-yl ether and 15% of neopentyl glycol mono-1,7,7-trimethyl-bicyclo[2.2.1-]hept-2-yl ether.

It was possible to separate off the monoether (boiling point: 104° C./0.3 mbar; viscous, colorless, odorless liquid) from the diether (boiling point: 165° C./0.3 mbar, viscous, colorless, odorless liquid) by distillation over a column.

EXAMPLE 12

272 g (2 moles) of camphene, 665 g (4 moles) of TCD-alcohol-M (mixture of 3- and 4-hydroxymethyl-tricyclo[$5.2.1.0^{2,6}$]decane (manufacturer Ruhrchemie, Oberhausen-Holten)) and 10 g of concentrated sulfuric acid were initially introduced into the apparatus described in Example 1. The mixture was warmed to 100° C. and was subsequently stirred at this temperature for 24 hours, the batch was washed with water in the presence of ether until neutral and, after the ether had been stripped off, the excess of TCD-alcohol was distilled off up to an internal temperature of 160° C. under a vacuum of 13 mbar. A brownish, odorless liquid which solidified at room temperature remained.

Yield: 450 g of 1,7,7-trimethyl-bicyclo[2.2.1]hept-2-yl (tricyclo[5.2.1.0$^{2,6}$]dec-3- and 4-yl)-methyl ether=74.5% of theory.

Melting point range: 70° to 80° C.
Molecular weight: 312; calculated: 302.

EXAMPLE 13

272 g (2 moles) of camphene and 546 g (3 moles) of 1-(3,3-dimethyl-bicyclo[2.2.1]hept-2-yl)-propan-2-ol was stirred in the presence of 12 g of p-toluenesulfonic acid at 120° C. for 48 hours in the apparatus described in Example 1. After washing with water and distilling off the highly volatile constituents up to an internal temperature of 135° C./0.06 mbar, a colorless, viscous liquid which had a pleasantly fruity smell and a density (20° C.) of 0.978 and distilled at 123° to 127° C. under 0.06 mbar was obtained.

Yield: 144 g of 1,7,7-trimethyl-bicyclo[2.2.1]hept-2-yl 1-(3,3-dimethyl-bicyclo[2.2.1]hept-2-yl)-prop-2-yl ether=22.6% of theory.

Molecular weight: 311; calculated; 318.
Gas chromatography: about 90% pure product.

EXAMPLE 14

136 g (1 mole) of camphene was stirred with 222 g (1 mole) of isolongifolol (=4,8,8-trimethyl-9-hydroxymethyl-decahydro-1,4-methano-azulene) in the presence of 5 g of boron trifluoride-diethyl etherate at 100° C. for 20 hours in the apparatus described in Example 1. After the customary working up, a yellowish residue which was solid at room temperature and smelt of wood remained. Colorless crystals with a woody smell were obtained by recrystallization.

Yield (after recrystallization): 147 g of 1,7,7-trimethylbicyclo[2.2.1]hept-2-ylisolongifolyl ether=41% of theory.

Melting point: 96° to 98° C.
Molecular weight: 356; calculated: 358.

We claim:
1. A terpene ether of the formula

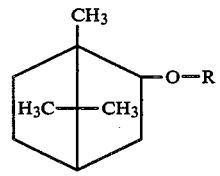

wherein R is a member of the group consisting of
2-(3,3-dimethyl-bicyclo[2.2.1]-hept-2-yl)-ethoxycyclohexyl,
4-(1,7,7-trimethyl-bicyclo[2.2.1]-hept-2-oxy-methyl)-cyclohexyl-1-methyl,
4-hydroxymethylcyclohexyl-1-methyl,
2-(2,2,3-trimethyl-cyclopent-1-yl)-ethyl,
(tricyclo[5.2.1.0$^{2,6}$]dec-3-yl)-methyl,
(tricyclo[5.2.1.0$^{2,6}$]dec-4-yl)-methyl,
1-(3,3-dimethyl-bicyclo[2.2.1]-hept-2-yl)-prop-2-yl
and isolongifolyl.

* * * * *